(12) United States Patent
Beardsley et al.

(10) Patent No.: US 7,368,559 B2
(45) Date of Patent: May 6, 2008

(54) FCγRIIA-SPECIFIC NUCLEIC ACID INTERFERENCE

(76) Inventors: Diana Beardsley, 129 Mill Rock Rd., Hamden, CT (US) 06517; Bing-Guan Chen, 84 Overbrook Rd., Madison, CT (US) 06443

( * ) Notice: Subject to any disclaimer, the term of this patent is extended or adjusted under 35 U.S.C. 154(b) by 0 days.

(21) Appl. No.: 10/989,597

(22) Filed: Nov. 15, 2004

(65) Prior Publication Data
US 2005/0250722 A1    Nov. 10, 2005

Related U.S. Application Data

(60) Provisional application No. 60/564,459, filed on Apr. 22, 2004, provisional application No. 60/519,899, filed on Nov. 14, 2003.

(51) Int. Cl.
| | |
|---|---|
| C07H 21/04 | (2006.01) |
| C07H 21/02 | (2006.01) |
| A61K 48/00 | (2006.01) |
| C12Q 1/68 | (2006.01) |

(52) U.S. Cl. .................. 536/24.5; 435/6; 435/325; 435/375; 514/44; 536/23.1; 536/24.3

(58) Field of Classification Search .................. None
See application file for complete search history.

(56) References Cited

FOREIGN PATENT DOCUMENTS

| WO | WO-96/40199 | | 12/1996 | | |
|---|---|---|---|---|---|
| WO | WO 96/40199 | * | 12/1996 | .................. | 514/44 |
| WO | WO 02/062954 A2 | * | 8/2002 | .................. | 514/44 |
| WO | WO-03/070912 | | 8/2003 | | |
| WO | WO 2004/052364 | | 6/2004 | | |
| WO | WO 2005/007623 | | 1/2005 | | |

OTHER PUBLICATIONS

Brooks et al., Structure and Expression of Human IgC FcRII(CD32), 1989, J. Exp. Med., vol. 170, pp. 1369-1385.*
Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Elbashir et al., Functional anatomy of siRNAs for mediating efficient RNAi in Drosophila melanogaster embryo lysate, 2001, The EMBO Journal, vol. 20, No. 23, pp. 6877-6888.*
Hammond et al., Post-Transcriptional Gene Silencing by Double-Stranded RNA, 2001, Nature Reviews, Genetics, vol. 2, pp. 110-119.*

Schmidt et al., Base and sugar requirements for RNA cleavage of essential nucleoside residues in internal loop B of the hairpin ribozyme: implications for secondary structure, 1996, Nucleic Acids Research, vol. 24, No. 4, pp. 573-581.*
International Preliminary Report on Patentability and Written Opinion. International Application: PCT/US2004/038192. Mailing date: May 26, 2006.
Takada et al., "Hydrogen Peroxide Activates NF-kB through Tyrosine Phosphorylation of IkBα and Serine Phosphorylation of p65," *Journal of Biological Chemistry* 278(26):24233-24241 (2003).
Stenton et al., "Aerosolized Syk Antisense Suppresses Syk Expression, Mediator Release from Macrophages, and Pulmonary Inflammation," *The Journal of Immunology* 164:3790-3797 (2000).
Matsuda et al., "Abrogation of the Feγ Receptor IIA-Mediated Phagocytic Signal by Stem-Loop Syk Antisense Oligonucleotides," *Molecular Biology of the Cell* 7:1095-1106 (1996.
Lim et al., "Flow Cytometric Monocyte Phagocytic Assay for Predicting Platelet Transfusion Outcome," *Transfusion* 42:309-316 (2002).
Takada et al., "TNF Activates Syk Protein Tyrosine Kinase Leading to TNF-induced MAPK Activation, NF-κB Activation, and Apoptosis," *The Journal of Immunology* 173:1066-1077 (2004).
Wiener et al., "Anti-HPA-1a-mediated platelet phagocytosis by monocytes in vitro and its inhibition by Fc gamma receptor (FcγR) reactive reagents," *European Journal of Haematology* 70:67-74 (2003).
Elbashir et al., "Duplexes of 21-nucleotide RNAs mediate RNA interference in cultured mammalian cells," *Nature* 411:494-498 (2001).
Gregory J. Hannon, "RNA interference," Nature 418:244-251 (2002).
Elbashir et al., "Functional anatomy of siRNAs for mediating efficient RNAi in *Drosophila melanogaster* embryo lysate," *The EMBO Journal* 20(23):6877-6888 (2001).
Paddison et al., "Short hairpin RNAs (shRNAs) induce sequence-specific silencing in mammalian cells," *Genes & Development* 16:948-958 (2002).
Soutschek et al., "Therapeutic silencing of an endogenous gene by systemic administration of modified siRNAs," *Nature* 432:173-178 (2004).
Beardsly et al., "Short interfering RNA sequence (RNAi) specific for Syk and FcγRIIA (CD32A) selectively inhibit antibody-mediated platelet phagocytosis by human macrophages," *Blood* 102(11):86a (2003).

* cited by examiner

*Primary Examiner*—Jon Eric Angell
*Assistant Examiner*—Amy H. Bowman
(74) *Attorney, Agent, or Firm*—Wolf, Greenfield & Sacks, P.C.

(57) ABSTRACT

The present invention provides methods and compositions for attenuating expression of FcγRIIA. In general, the described methodology involves the use of RNAi constructs that are targeted to a FcγRIIA mRNA sequence.

8 Claims, 3 Drawing Sheets

*1: Mock-treated THP-1 cells;  *2: Control siRNA transfected THP-1 cells; A-L: Individual CD32A siRNA transfected THP-1 cells.

A: Control without anti-platelet antibody; B: THP-1 with antibody-coated platelet; C: Mock-treated THP-1 with antibody-coated platelets; D: Control-siRNA treated THP-1 with antibody-coated platelets; E, F, G: Individual CD32A-siRNA (e,f,h) treated THP-1 with antibody-coated platelets; H: Syk-siRNA treated THP-1 with antibody-coated platelets.

SEQUENCE LISTING

```
<160> NUMBER OF SEQ ID NOS: 13

<210> SEQ ID NO 1
<211> LENGTH: 2411
<212> TYPE: DNA
<213> ORGANISM: Homo sapiens

<400> SEQUENCE: 1
gtctcttaaa acccactgga cgttggcaca gtgctgggat gactatggag acccaaatgt      60
ctcagaatgt atgtcccaga aacctgtggc tgcttcaacc attgacagtt ttgctgctgc     120
tggcttctgc agacagtcaa gctgctcccc caaaggctgt gctgaaactt gagccccgt     180 ggatcaacgt gctccaggag gactctgtga ctctgacatg ccaggggct cgcagccctg     240 agagcgactc cattcagtgg ttccacaatg ggaatctcat tcccacccac acgcagccca     300
gctacaggtt caaggccaac aacaatgaca gcggggagta cacgtgccag actggccaga     360
ccagcctcag cgaccctgtg catctgactg tgctttccga atggctggtg ctccagaccc     420
ctcacctgga gttccaggag ggagaaacca tcatgctgag gtgccacagc tggaaggaca     480
agcctctggt caaggtcaca ttcttccaga atggaaaatc ccagaaattc tcccatttgg     540
atcccacctt ctccatccca caagcaaacc acagtcacag tggtgattac cactgcacag     600
gaaacatagg ctacacgctg ttctcatcca gcctgtgac catcactgtc caagtgccca     660
gcatgggcag ctcttcacca atggggatca ttgtggctgt ggtcattgcg actgctgtag     720
cagccattgt tgctgctgta gtggccttga tctactgcag gaaaaagcgg atttcagcca     780
attccactga tcctgtgaag gctgcccaat ttgagccacc tggacgtcaa atgattgcca     840
tcagaaagag acaacttgaa gaaaccaaca atgactatga aacagctgac ggcggctaca     900
tgactctgaa ccccagggca cctactgacg atgataaaaa catctacctg actcttcctc     960
ccaacgacca tgtcaacagt aataactaaa gagtaacgtt atgccatgtg gtcatactct    1020
cagcttgctg agtggatgac aaaaagaggg gaattgttaa aggaaaattt aaatggagac    1080
tggaaaaatc ctgagcaaac aaaaccacct ggcccttaga aatagcttta actttgctta    1140
aactacaaac acaagcaaaa cttcacgggg tcatactaca tacaagcata agcaaaactt    1200
aacttggatc atttctggta aatgcttatg ttagaaataa gacaaccca gccaatcaca    1260 agcagcctac taacatataa ttaggtgact agggactttc taagaagata cctaccccca    1320
aaaaacaatt atgtaattga aaaccaaccg attgcctta ttttgcttcc acattttccc    1380
aataaatact tgcctgtgac attttgccac tggaacacta aacttcatga attgcgcctc    1440 agattttttcc tttaacatct tttttttttt tgacagagtc tcaatctgtt acccaggctg    1500
gagtgcagtg gtgctatctt ggctcactgc aaacccgcct cccaggttta agcgattctc    1560
atgcctcagc ctcccagtag ctgggattag aggcatgtgc catcatacc agctaatttt    1620 tgtatttttt attttttttt tttagtagag acagggtttc gcaatgttgg ccaggccgat    1680
ctcgaacttc tggcctctag cgatctgccc gcctcggcct cccaaagtgc tgggatgacc    1740
```

```
agcatcagcc ccaatgtcca gcctctttaa catcttcttt cctatgccct ctctgtggat    1800
ccctactgct ggtttctgcc ttctccatgc tgagaacaaa atcacctatt cactgcttat    1860
gcagtcggaa gctccagaag aacaaagagc ccaattacca gaaccacatt aagtctccat    1920
tgttttgcct tgggatttga aagagaatt agagaggtga ggatctggta tttcctggac    1980
taaattcccc ttggggaaga cgaagggatg ctgcagttcc aaaagagaag gactcttcca    2040
gagtcatcta cctgagtccc aaagctccct gtcctgaaag ccacagacaa tatggtccca    2100
aatgactgac tgcaccttct gtgcctcagc cgttcttgac atcaagaatc ttctgttcca    2160
catccacaca gccaatacaa ttagtcaaac cactgttatt aacagatgta gcaacatgag    2220
aaacgcttat gttacaggtt acatgagagc aatcatgtaa gtctatatga cttcagaaat    2280
gttaaaatag actaacctct aacaacaaat taaagtgat tgtttcaagg tgatgcaatt    2340
attgatgacc tattttattt ttctataatg atcatatatt acctttgtaa taaaacatta    2400
taaccaaaac a                                                         2411
```

<210> SEQ ID NO 2
<211> LENGTH: 21
<212> TYPE: DNA
<213> ORGANISM: Homo sapiens

<400> SEQUENCE: 2
aaacttgagc ccccgtggat c     21

<210> SEQ ID NO 3
<211> LENGTH: 21
<212> TYPE: DNA
<213> ORGANISM: Homo sapiens

<400> SEQUENCE: 3
aatttgagcc acctggacgt c     21

<210> SEQ ID NO 4
<211> LENGTH: 21
<212> TYPE: DNA
<213> ORGANISM: Homo sapiens

<400> SEQUENCE: 4
aaagagacaa cttgaagaaa c     21

<210> SEQ ID NO 5
<211> LENGTH: 21
<212> TYPE: DNA
<213> ORGANISM: Homo sapiens

<400> SEQUENCE: 5
aaaccatcat gctgaggtgc c     21

<210> SEQ ID NO 6
<211> LENGTH: 21
<212> TYPE: DNA
<213> ORGANISM: Homo sapiens

<400> SEQUENCE: 6
aaccatcatg ctgaggtgcc a     21

<210> SEQ ID NO 7
<211> LENGTH: 21
<212> TYPE: DNA

-continued

```
<213> ORGANISM: Homo sapiens

<400> SEQUENCE: 7
aaattctccc gtttggatcc c                                              21

<210> SEQ ID NO 8
<211> LENGTH: 21
<212> TYPE: DNA
<213> ORGANISM: Homo sapiens

<400> SEQUENCE: 8
aattctcccg tttggatccc a                                              21

<210> SEQ ID NO 9
<211> LENGTH: 21
<212> TYPE: DNA
<213> ORGANISM: Homo sapiens

<400> SEQUENCE: 9
aaacccgcct cccaggttta a                                              21

<210> SEQ ID NO 10
<211> LENGTH: 21
<212> TYPE: DNA
<213> ORGANISM: Homo sapiens

<400> SEQUENCE: 10
aacttctggc ctctagcgat c                                              21

<210> SEQ ID NO 11
<211> LENGTH: 21
<212> TYPE: DNA
<213> ORGANISM: Homo sapiens

<400> SEQUENCE: 11
aagtgctggg atgaccagca t                                              21

<210> SEQ ID NO 12
<211> LENGTH: 21
<212> TYPE: DNA
<213> ORGANISM: Homo sapiens

<400> SEQUENCE: 12
aatgtccagc ctctttaaca t                                              21

<210> SEQ ID NO 13
<211> LENGTH: 21
<212> TYPE: DNA
<213> ORGANISM: Homo sapiens

<400> SEQUENCE: 13
aacatcttct ttcctatgcc c                                              21
```

FCγRIIA-SPECIFIC NUCLEIC ACID INTERFERENCE

CROSS-REFERENCE TO RELATED APPLICATIONS

This application claims the benefit of the filing date of U.S. Provisional Application No. 60/519,899, filed Nov. 14, 2003, entitled "Inhibition of phagocytosis with RNAi specific for cell surface receptors", and of U.S. Provisional Application No. 60/564,459, filed Apr. 22, 2004, entitled "Short interfacing (si) RNA sequence(s) specific for the SH2 tyrosine kinase, Syk, inhibits phagocytosis by human macrophages". The teachings of both of the above-mentioned applications are incorporated by reference herein in their entirety.

BACKGROUND OF THE INVENTION

Immunoglobulins are typically composed of two fundamental domains, the constant domain (Fc) and the variable domain. While the variable domain interacts with target antigens, the constant domain mediates a variety of biological events by interacting with other proteins of the host organism. Receptors for the Fc portion of IgG, Fcγ receptors, play an essential role in the protection of the organism against foreign antigens by removing antigen-antibody complexes from the circulation. Receptors are present on monocytes, macrophages, neutrophils, natural killer (NK) cells, platelets, and T and B lymphocytes, and they participate in diverse functions such as phagocytosis of immune complexes, NK cell ADCC, platelet activation, and modulation of antibody production by B cells.

Fcγ receptors also play a role in a number of diseases characterized by a hyperactive immune system or other undesirable immunological activity. Fcγ receptors participate in a number of autoimmune and inflammatory diseases. As an example, Fcγ receptors are implicated in immune thrombocytopenia. The pathogenic mechanism of immune thrombocytopenia involves antibody-mediated destruction of platelets in the reticuloendothelial system through Fcγ receptors (FcγRs) expressed on tissue macrophages, particularly in the spleen and liver. FcγRs signal via immunoreceptor tyrosine-based activation motifs (ITAMs) that are located either in the cytosolic domains of the receptors themselves (FcγRIIA), or within associated γ (FcγRI and FcγRIIIA) or ζ (FcγRIIIA) subunits. Following clustering of the FcγRs and their associated γ subunits by bound IgG ligands, tyrosine residues within the ITAMs become phosphorylated. The tyrosine-phosphorylated residues of the ITAMs serve as high affinity binding sites for Syk, a tyrosine kinase that contains tandem SH2 domains, which propagates intracellular signaling processes. In humans, FcγRIIA and FcγRIII are the primary activating receptors.

The FcγRIIB receptor has an inhibitory role. FcγRIIB recruits the SHIP kinase and abrogates signaling triggered by activating Fcγ receptors. The overall cellular response depends in part on the ratio of signaling mediated by inhibiting and activating receptors.

An object of the present disclosure is to provide nucleic acid agents that inhibit FcγRIIA expression and to provide methods of using such agents for therapeutic purposes.

SUMMARY OF THE INVENTION

The disclosure provides, in part, RNAi constructs that target FcγRIIA and decrease FcγRIIA expression. Such constructs may be used in essentially any method where it is desirable to decrease the level of FcγRIIA protein. In particular, the disclosed nucleic acids will be useful in treating various disorders related to immune system function, such as immune thrombocytopenia, heparin-induced thrombocytopenia and asthma.

In certain aspects, the disclosure provides RNAi constructs for inhibiting the expression of FcγRIIA. Such nucleic acids may comprise (a) an antisense polynucleotide strand that hybridizes to at least a portion of a FcγRIIA transcript and inhibits FcγRIIA expression; and (b) a sense polynucleotide that hybridizes to said antisense polynucleotide. The antisense and sense strands may be two separate nucleic acid strands, or the strands may be joined by a linker or by a stretch of further nucleic acid. For example, the RNAi construct may be a single stranded nucleic acid containing two regions that are complementary, thereby forming a hairpin nucleic acid with a stretch of double-stranded helix. Such hairpin nucleic acids are often processed into an siRNA inside a cell. Optionally, the portion of the nucleic acid that forms a double helix is about 19 to about 23 base pairs in length. The antisense polynucleotide strand may be complementary to a sequence of the human FcγRIIA mRNA of SEQ ID NO:1, or that of another animal of interest. The RNAi construct may be designed so as to have little or no effect on FcγRIIB expression. For example, the antisense strand may be designed to have no more than 15 consecutive nucleotides that are complementary to an FcγRIIB mRNA sequence, and preferably the antisense strand has no more than 10, no more than 5, or no more than 3 consecutive nucleotides that are complementary to an FcγRIIB mRNA sequence. The antisense polynucleotide strand may be complementary to at least 5, 6, 7, 8, 10, 15, 20 or more nucleotides of a sequence selected from the group consisting of: SEQ ID Nos. 4 through 13. The antisense polynucleotide may consist of a sequence that is complementary to a sequence selected from the group consisting of: SEQ ID Nos. 4-13. The sense and antisense strands may be essentially any suitable nucleic acid, including RNA, DNA or other nucleic acid species that are not readily categorized as DNA or RNA. The sense and antisense strands need not be formed of the same nucleic acids. Either or both strands may include one or more modifications to the typical nucleic acid structure. For example, the antisense strand may comprise one or more of the following modifications: (a) a modification to the sugar-phosphate backbone; (b) a modification to a base portion of a nucleotide; and (c) a conjugated hydrophobic moiety. The sense strand may be similarly modified.

RNAi constructs may be formulated for administration to an organism. A pharmaceutical preparation for delivery of an RNAi construct to an organism may comprise a pharmaceutically acceptable carrier and an RNAi construct that inhibits expression of FcγRIIA. The preparation may be suitable for any desirable mode of administration. In certain instances, such as for the treatment of asthma or other disorders of the airway system, the preparation may be designed for administration by inhalation (e.g., aerosolized or intranasal).

In certain aspects, the disclosure provides methods for decreasing expression of FcγRIIA in a cell. Such methods may comprise contacting the cell with a composition comprising an RNAi construct that inhibits FcγRIIA expression.

In certain aspects, the disclosure provides methods for decreasing expression of FcγRIIA in one or more cells of an individual. Such methods may comprise administering to the individual a composition comprising a double-stranded nucleic acid that inhibits FcγRIIA expression. The individual may be diagnosed with a condition associated with excess Fc receptor activity or with any of a variety of disorders related to the immune system, such as asthma, immune thrombocytopenia or an autoimmune disease.

In an additional aspect, the disclosure provides improved assays for measuring phagocytosis of target material in phagocytic cells. The methods employ phagocytic cells from a cell line, particularly a cell of a hematopoietic lineage, such a monoblastic cell line or other immune cell line. Desirable cells will generally express one or more Fcγ receptors that mediate phagocytosis of opsonized material, such as FcγRIIA. A method may comprise (a) exposing target material to antibody to generate prepared target material; (b) exposing the phagocytic cells to the prepared target material; and (c) selectively detecting the prepared target material that is internalized by the phagocytic cells. The target material will often be cells, particularly platelets. However, phagocytic cells are generally take up materials non-specifically, and therefore other materials, such as microbeads, may be used as a target material. Target material may be labeled in a variety of ways to facilitate detection, and target material may be pre-labeled or labeled upon exposure to antibody. The label may, for example, be a fluorescent label. In a preferred embodiment, the label is a fluorescent label, and selectively detecting the prepared target material comprises selectively quenching any extracellular label. Thus, detection of the fluorescent signal necessarily detects signal from unquenched fluorophore within the phagocytic cells.

DETAILED DESCRIPTION OF THE INVENTION

I. RNAi Constructs

Figure 1:
FIG. 1: A diagram comparing the sequences of human FcγRIIA and FcγRIIB, showing the location of probes for Northern blots that distinguish between the two transcripts.
Figure 1:
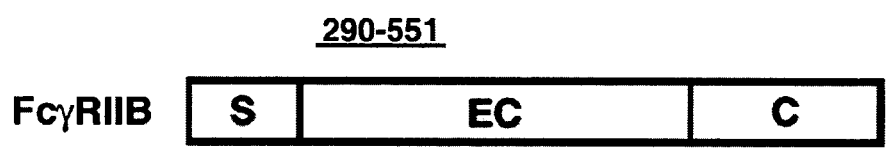
Figure 2:
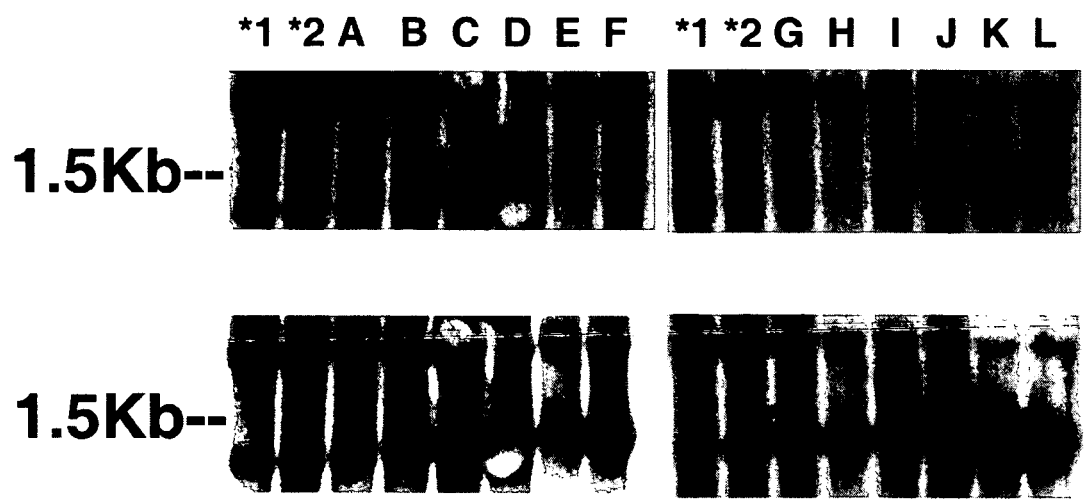
FIG. 2: Using probes designed to hybridize with FcγRIIA only, or designed to hybridize with both FcγRIIA and FcγRIIB, siRNA transfection of THP-1 cells was shown to allow the selective knockdown of FcγRIIA.

In part, the disclosure provides RNA interference ("RNAi") constructs that are useful for inhibiting FcγRIIA expression. As used herein, the term "RNAi construct" is a generic term used to include any of the various nucleic acid reagents that can be used to achieve a decrease in the levels of a targeted protein. Such decrease, however achieved, shall be referred to herein as a decrease in "expression" of the protein. While not wishing to be bound to any particular mechanism, it is expected that such constructs will act by an RNA interference ("RNAi") mechanism. Such constructs may be, for example, small interfering RNAs (siRNAs), hairpin RNAs, and other RNA species which can be cleaved in vivo to form siRNAs. As will be apparent from the preceding examples, an RNAi construct may include a single nucleic acid molecule, as in the case of hairpin RNAs, or two nucleic acid molecules, as in the case of siRNAs, or more nucleic acid molecules. Nonetheless, an RNAi construct will generally include at least some portion in which, under physiological conditions, a double helix is formed, where such double helix may result from intramolecular hybridization or intermolecular hybridization. Although RNAi is a term that was initially applied only with respect to RNA molecules, it is now understood that the same effect may be accomplished with modified nucleic acids that are not necessarily RNA, and also with molecules containing one or more DNA moieties. Constructs including any of the various nucleic acids are intended to be included in the term "RNAi construct".

As used herein, the term "nucleic acid" refers to polynucleotides such as deoxyribonucleic acid (DNA) and ribonucleic acid (RNA). The term should also be understood to include, as applicable to the embodiment being described, single-stranded (such as sense or antisense) and double-stranded polynucleotides. The "canonical" nucleotides are adenosine (A), guanosine (G), cytosine (C), thymidine (T), and uracil (U), and include a ribose-phosphate backbone, but the term nucleic acid is intended to include polynucleotides comprising only canonical nucleotides as well as polynucleotides including one or more modifications to the sugar phosphate backbone or the nucleoside. DNA and RNA are chemically different because of the absence or presence of a hydroxyl group at the 2' position on the ribose. Modified nucleic acids exist that cannot be readily termed DNA or RNA (e.g. in which an entirely different moiety is positioned at the 2' position), as do functional analogs, such as peptide nucleic acids (PNAs) in which the backbone is a peptide backbone, in which the backbone contains neither sugar nor phosphate. All such molecules are included in the term "nucleic acid". An "unmodified" nucleic acid is a nucleic acid that contains only canonical nucleotides and a DNA or RNA backbone.

RNA interference is a phenomenon describing double-stranded nucleic acid-dependent gene specific posttranscriptional silencing. Initial attempts to harness this phenomenon for experimental manipulation of mammalian cells were foiled by a robust and nonspecific antiviral defense mechanism activated in response to long dsRNA molecules. Gil et al. *Apoptosis* 2000, 5:107-114. The field was significantly advanced upon the demonstration that synthetic duplexes of 21 nucleotide RNAs could mediate gene specific RNAi in mammalian cells, without invoking generic antiviral defense mechanisms. Elbashir et al. *Nature* 2001, 411:494-498; Caplen et al. *Proc Natl Acad Sci* 2001, 98:9742-9747. As a result, small-interfering RNAs (siRNAs) have become powerful tools to dissect gene function, and data from Soutscheck et al. Nature 2004, 432:173-178 has established that double-stranded RNA constructs can be delivered in vivo to modulate expression of the target gene.

The mRNA sequence for human FcγRIIA (also known as CD32A and FCGR2A) is represented below:

```
Human FcγRIIA mRNA (Genbank NM_021642; gi:50511935; SEQ ID NO:1)
  1 gtctcttaaa acccactgga cgttggcaca gtgctgggat gactatggag acccaaatgt 61 ctcagaatgt atgtcccaga aacctgtggc tgcttcaacc attgacagtt ttgctgctgc
```

-continued

```
 121 tggcttctgc agacagtcaa gctgctcccc caaaggctgt gctgaaactt gagcccccgt
 181 ggatcaacgt gctccaggag gactctgtga ctctgacatg ccaggggct cgcagccctg
 241 agagcgactc cattcagtgg ttccacaatg ggaatctcat tcccacccac acgcagccca
 301 gctacaggtt caaggccaac aacaatgaca gcggggagta cacgtgccag actggccaga
 361 ccagcctcag cgaccctgtg catctgactg tgctttccga atggctggtg ctccagaccc
 421 ctcacctgga gttccaggag ggagaaacca tcatgctgag gtgccacagc tggaaggaca
 481 agcctctggt caaggtcaca ttcttccaga atggaaaatc ccagaaattc tcccatttgg
 541 atcccacctt ctccatccca caagcaaacc acagtcacag tggtgattac cactgcacag
 601 gaaacatagg ctacacgctg ttctcatcca gcctgtgac catcactgtc caagtgccca
 661 gcatgggcag ctcttcacca atggggatca ttgtggctgt ggtcattgcg actgctgtag
 721 cagccattgt tgctgctgta gtggccttga tctactgcag gaaaaagcgg atttcagcca
 781 attccactga tcctgtgaag gctgcccaat ttgagccacc tggacgtcaa atgattgcca
 841 tcagaaagag acaacttgaa gaaaccaaca atgactatga aacagctgac ggcggctaca
 901 tgactctgaa ccccagggca cctactgacg atgataaaaa catctacctg actcttcctc
 961 ccaacgacca tgtcaacagt aataactaaa gagtaacgtt atgccatgtg gtcatactct
1021 cagcttgctg agtggatgac aaaaagaggg gaattgttaa aggaaaattt aaatggagac
1081 tggaaaaatc ctgagcaaac aaaaccacct ggcccttaga aatagcttta actttgctta
1141 aactacaaac acaagcaaaa cttcacgggg tcatactaca tacaagcata agcaaaactt
1201 aacttggatc atttctggta aatgcttatg ttagaaataa dacaaccca gccaatcaca
1261 agcagcctac taacatataa ttaggtgact agggactttc taagaagata cctaccccca
1321 aaaaacaatt atgtaattga aaaccaaccg attgccttta ttttgcttcc acatttccc
1381 aataaatact tgcctgtgac attttgccac tggaacacta aacttcatga attgcgcctc
1441 agatttttcc tttaacatct tttttttttt tgacagagtc tcaatctgtt acccaggctg
1501 gagtgcagtg gtgctatctt ggctcactgc aaacccgcct cccaggttta agcgattctc
1561 atgcctcagc ctcccagtag ctgggattag aggcatgtgc catcataccc agctaatttt
1621 tgtaaaaaaa atttttttttt tttagtagag acagggtttc gcaatgttgg ccaggccgat
1681 ctcgaacttc tggcctctag cgatctgccc gcctcggcct cccaaagtgc tgggatgacc
1741 agcatcagcc ccaatgtcca gcctctttaa catcttcttt cctatgccct ctctgtggat
1801 ccctactgct ggtttctgcc ttctccatgc tgagaacaaa atcacctatt cactgcttat
1861 gcagtcggaa gctccagaag aacaaagagc ccaattacca gaaccacatt aagtctccat
1921 tgttttgcct tgggatttga gaagagaatt agagaggtga ggatctggta tttcctggac
1981 taaattcccc ttggggaaga cgaagggatg ctgcagttcc aaaagagaag gactcttcca
2041 gagtcatcta cctgagtccc aaagctccct gtcctgaaag ccacagacaa tatggtccca
2101 aatgactgac tgcaccttct gtgcctcagc cgttcttgac atcaagaatc ttctgttcca
2161 catccacaca gccaatacaa ttagtcaaac cactgttatt aacagatgta gcaacatgag
2221 aaacgcttat gttacaggtt acatgagagc aatcatgtaa gtctatatga cttcagaaat
2281 gttaaaatag actaacctct aacaacaaat taaagtgat tgtttcaagg tgatgcaatt
2341 attgatgacc tattttatttt ttctataatg atcatatatt acctttgtaa taaaacatta
2401 taaccaaaac a
```

Suitable nucleic acid constructs may be designed by selecting a target region of a FcγRIIA mRNA sequence, such as that of the human, listed above or other animal, and preparing a construct having a polynucleotide strand that hybridizes to the selected region of the mRNA (the "antisense strand") and a polynucleotide that hybridizes to the antisense strand (the "sense strand"). Constructs designed at random are unlikely to inhibit FcγRIIA expression. While it is possible to screen through large numbers of such constructs to identify those that are effective, it is generally desirable to follow a procedure for selecting target regions that have an improved likelihood of success.

For example, one may employ the algorithm of Elbashir et al. (EMBO J. 20: 6877-6888, 2001) to select an appropriate target region and generate a construct with a higher chance of being effective. Briefly, this approach involves identifying nucleotide sequences in the target mRNA that begin with an AA dinucleotide and have a length of 21 nucleotides. siRNAs with other 3' terminal dinucleotide overhangs have been shown to effectively induce RNAi, although overhang sequences containing a GG dinucleotide may be cleaved by RNAse.

Double-stranded nucleic acid constructs may be evaluated for effectiveness by administering the construct to a cell and evaluating the effect on FcγRIIA protein levels, kinase activity or another feature that is correlated with FcγRIIA expression. Different nucleic acid constructs will tend to affect FcγRIIA expression to different degrees, and it will not always be apparent what percent inhibition of FcγRIIA expression will achieve the desired effects. Accordingly, double-stranded nucleic acid constructs may also be evaluated for effectiveness in one or more bioassays. For example, FcγRIIA-targeted constructs may be tested for effects on antibody mediated platelet phagocytosis to assess the effect on Fcγ-mediated events. Examples of such assays are provided below.

The FcγRIIA mRNA sequence is closely related to that of the FcγRIIB mRNA sequence. However, while FcγRIIA is an activating receptor, FcγRIIB is an inhibiting receptor. Accordingly, it is desirable to selectively interfere with FcγRIIA, while leaving FcγRIIB unaffected. RNAi constructs disclosed herein may be designed to have this type of selectivity. Notably, such selectivity has not, to our knowledge, been achieved previously by antibody-based inhibition or by inhibition using traditional antisense techniques. The 3' end of the FcγRIIA transcript is particularly divergent from that of FcγRIIB, as shown schematically in FIG. 1. An RNAi construct selective for FcγRIIA may be designed to have few or no consecutive nucleic acids in the antisense strand that are complementary to FcγRIIB transcript. For example, the antisense strand may be designed to have no more than 15 consecutive nucleotides that are complementary to an FcγRIIB mRNA sequence, and preferably the antisense strand has no more than 10, no more than 5, or no more than 3 consecutive nucleotides that are complementary to an FcγRIIB mRNA sequence. However, a small number of complementary nucleic acids may be included and yet have no significant effect on FcγRIIB transcript. Such effects may be evaluated empirically, by, for example, transcript specific Northern blotting or RT-PCR. Examples of human FcγRIIB mRNA sequences for comparison may be found in Genbank entries NM_001002273; NM_004001; NM_001002275; NM_001002274.

The table below lists the target sequences (sense DNA) for a series of RNA interference constructs designed to inhibit FcγRIIA expression.

TABLE 1

Human FcγRIIA siRNA Target Sequences

| | | |
|---|---|---|
| CD32IIA-A | AAACTTGAGCCCCCGTGGATC | (SEQ ID NO:2) |
| CD32IIA-B | AATTTGAGCCACCTGGACGTC | (SEQ ID NO:3) |
| CD32IIA-C | AAAGAGACAACTTGAAGAAAC | (SEQ ID NO:4) |
| CD32IIA-D | AAACCATCATGCTGAGGTGCC | (SEQ ID NO:5) |
| CD32IIA-E | AACCATCATGCTGAGGTGCCA | (SEQ ID NO:6) |
| CD32IIA-F | AAATTCTCCCGTTTGGATCCC | (SEQ ID NO:7) |
| CD32IIA-G | AATTCTCCCGTTTGGATCCCA | (SEQ ID NO:8) |
| CD32IIA-H | AAACCCGCCTCCCAGGTTTAA | (SEQ ID NO:9) |
| CD32IIA-I | AACTTCTGGCCTCTAGCGATC | (SEQ ID NO:10) |
| CD32IIA-J | AAGTGCTGGGATGACCAGCAT | (SEQ ID NO:11) |
| CD32IIA-K | AATGTCCAGCCTCTTTAACAT | (SEQ ID NO:12) |
| CD32IIA-L | AACATCTTCTTTCCTATGCCC | (SEQ ID NO:13) |

As demonstrated herein, RNAi constructs containing an antisense strand that hybridizes to a sequence of any of SEQ ID Nos. 4-13 are effective in reducing FcγRIIA transcript levels. See Example 1, Table 2. RNAi constructs containing an antisense strand that hybridizes to a sequence of any of SEQ ID Nos. 10-13 are effective in reducing FcγRIIA transcript levels by greater than 30%, while those containing an antisense strand that hybridizes to a sequence of any of SEQ ID Nos. 6, 7, and 9 are effective in reducing FcγRIIA protein levels by greater than 60%. RNAi constructs containing an antisense strand that hybridizes to a sequence of any of SEQ ID Nos. 4, 6, 7, 8 and 9 are effective in reducing phagocytosis of opsonized platelets, while those containing an antisense strand that hybridizes to a sequence of any of SEQ ID Nos. 8 and 9 are effective in reducing phagocytosis of opsonized platelets by greater than 30%. Where an RNAi construct is to be used for a purpose related to reducing phagocytosis by immune cells, it may be preferable to use an RNAi construct that produces an effect in a phagocytosis bioassay, such as an RNAi construct having an antisense strand that hybridizes to a sequence of any of SEQ ID Nos. 4, 6, 7, 8 and 9. Where an RNAi construct is to be used for a purpose not related to reducing phagocytosis in immune cells, it may be preferable to use an RNAi construct that causes a measurable decrease in FcγRIIA levels, such as an RNAi construct containing an antisense strand that hybridizes to a sequence of any of SEQ ID Nos. 4-13. RNAi constructs containing an antisense strand that hybridizes to a sequence of SEQ ID No. 9 are particularly notable for having a strong effect on FcγRIIA levels and on platelet phagocytosis.

RNAi constructs may be designed to contain a nucleotide sequence that hybridizes under physiologic conditions of the cell to the nucleotide sequence of at least a portion of the mRNA transcript for the gene to be inhibited (i.e., the "target" gene) and is sufficient for decreasing the expression of the protein encoded by the target gene. The nucleotide sequence of the RNAi construct may hybridize to coding or non-coding portions of a transcript, including, for example, the 3' and 5' untranslated regions ("UTRs"). The RNAi construct need only be sufficiently similar to natural RNA that it has the ability to be effective. Thus, sequence variations that might be expected due to genetic mutation, strain polymorphism or evolutionary divergence may be tolerated. In certain cases, the number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA antisense strand do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the interfering RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro.

One or both strands of an RNAi construct may include modifications to the phosphate-sugar backbone and/or the nucleoside. In general, the sense strand does not directly participate in the formation of a silencing complex (RISC) and is therefore subject to few constraints in the number and type of modifications that may be introduced. The sense strand need only retain the ability to hybridize with the antisense strand, and, in the case of longer nucleic acids, should not interfere with the activity of RNAses, such as Dicer, that participate in cleaving longer double-stranded constructs to yield smaller, active siRNAs. The antisense strand should retain the ability to hybridize with both the sense strand and the target transcript, and the ability to form an RNAi induced silencing complex (RISC). Optionally, the sense strand comprises at least 20%, 30%, 50%, 70%, 90% and 100% modified nucleic acids. Optionally, the antisense strand comprises no more than 0%, 10%, 20%, 30%, 40% or 50% modified nucleic acids. Modifications may be useful for, e.g., reduced susceptibility to nucleases, improved bioavailability, improved formulation characteristics, and changed pharmacokinetic properties. Many nucleases are progressive enzymes that initiate degradation at one end of a nucleic acid. Therefore, resistance to nucleases may be conferred by modification of, for example, one, two, three or more nucleotides at either the 5'end, the 3'end or both ends of a sense or antisense strand. For example, one, two or three phosphorothioate linkages may be positioned at either the 5'end, the 3'end or both ends of a sense or antisense strand. As another example, one, two or three 2' O-methyl modified nucleotides may be positioned at either the 5'end, the 3'end or both ends of a sense or antisense strand. For a demonstration of the effectiveness of such modifications in improving the in vivo performance of RNAi constructs see, for example, Soutscheck et al. Nature 2004, 432:173-178. Nucleotides in the sense strand may also be DNA.

Methods of chemically modifying RNA molecules can be adapted for modifying RNAi constructs (see, for example, Heidenreich et al. (1997) *Nucleic Acids Res*, 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). Additional modified nucleotides are as follows (this list contains forms that are modified on either the backbone or the nucleoside or both, and is not intended to be all-inclusive): 2'-O-Methyl-2-aminoadenosine; 2'-O-Methyl-5-methyluridine; 2'-O-Methyladenosine; 2'-O-Methylcytidine; 2'-O-Methylguanosine; 2'-O-Methyluridine; 2-Amino-2'-deoxyadenosine; 2-Aminoadenosine; 2-Aminopurine-2'-deoxyriboside; 4-Thiothymidine; 4-Thiouridine; 5-Methyl-2'-deoxycytidine; 5-Methylcytidine; 5-Methyluridine; 5-Propynyl-2'-deoxycytidine; 5-Propynyl-2'-deoxyuridine; N1-Methyladenosine; N1-Methylguanosine; N2-Methyl-2'-deoxyguanosine; N6-Methyl-2'-deoxyadenosine; N6-Methyladenosine; O6-Methyl-2'-deoxyguanosine; and O6-Methylguanosine.

The double-stranded structure may be formed by a single self-complementary nucleic acid strand or by two complementary nucleic acid strands. A double-stranded nucleic acid disclosed herein may include portions of single-stranded nucleic acid. Duplex formation may be initiated either inside or outside the cell. The RNAi construct may be introduced in an amount that allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject nucleic acid constructs are "small interfering RNAs" or "siRNAs." These nucleic acids include an antisense RNA strand that is from about 19 to about 30 nucleotides in length, and possibly from about 21 to 23 nucleotides in length, e.g., corresponding in length to the fragments generated by nuclease "dicing" of long double-stranded RNAs. siRNAs may include a sense strand that is RNA, DNA or other modified nucleic acids. The siRNAs are understood to recruit nuclease complexes and guide the complexes to the target mRNA by pairing to the specific sequences. As a result, the target mRNA is degraded by the nucleases in the protein complex.

SiRNA molecules can be obtained using a number of techniques known to those of skill in the art. For example, the siRNA can be chemically synthesized or recombinantly produced using methods known in the art. For example, short sense and antisense oligomers can be synthesized and annealed to form double-stranded structures with 2-nucleotide overhangs at each end (Caplen, et al. (2001) *Proc Natl Acad Sci USA,* 98:9742-9747; Elbashir, et al. (2001) EMBO J, 20:6877-88). These double-stranded siRNA structures can then be introduced into cells, either by passive uptake or a delivery system of choice, such as described below.

In certain embodiments, the siRNA constructs can be generated by the processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. In this embodiment, modifications should be selected so as to not interfere with the activity of the RNAse.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, at least one strand of an siRNA has a 3' overhang consisting of from about 1 to about 6 nucleotides. The overhang may consist of from about 2 to about 4 nucleotides. Typically, the 3' overhangs consist of about 1 to about 3 nucleotides. In certain embodiments, one strand has a 3' overhang and the other strand is either blunt-ended or also has a 3' overhang. The length of the overhangs may be the same or different for each strand. In order to further enhance the stability of the siRNA, the 3' overhangs can be stabilized against degradation. In one embodiment, the RNA antisense strand is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

A sense or antisense strand may be conjugated to one or more additional moieties to improve properties such as stability, cellular uptake or pharmacokinetics. Hydrophobic moieties, such as lipids and sterols, such as cholesterol, may be conjugated to a sense or antisense strand. See for example, Lorenz et al. Bioorg. Med. Chem. Lett. 14, 4975-4977 (2004) and Soutscheck et al. Nature 2004, 432:173-178. A sense or antisense strand may include one, two, three or more such hydrophobic moieties.

In certain embodiments, an RNAi construct is in the form of a hairpin structure. The hairpin can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; McManus et al., *RNA,* 2002, 8:842-50; Yu et al., *Proc Natl Acad Sci USA,* 2002, 99:6047-52). Preferably, such hairpin RNAs are engineered in cells or in an animal to ensure continuous and stable suppression of a desired gene. It is known in the art that siRNAs can be produced by the processing of a hairpin RNA in the cell. In such an embodiment, the single strand portion connecting the sense and antisense portions should be designed so as to be cleavable by nucleases in vivo, and any duplex portion should be susceptible to processing by nucleases such as Dicer.

II. Methods for Using FcγRIIA-Targeted Interfering Nucleic Acids

RNAi acid constructs disclosed herein may be used in essentially any in vivo or in vitro setting where inhibition of FcγRIIA expression is desirable.

In human patients and other mammals, FcγRIIA-targeted nucleic acid constructs may be used to treat a variety of diseases related to the immune system. For example, FcγRIIA inhibition may be useful in the treatment of autoimmune diseases, particularly those characterized by interactions of immune complexes (eg, IgG-containing immune complexes) with Fc receptors (for example, those present on the surface of macrophages). Diseases such as immune cytopenias (e.g. immune thrombocytopenia, immune hemolytic anemia, or immune neutropenia), Guillain-Barre syndrome, myasthenia gravis, anti-Factor VIII immune disease, dermatomyositis, vasculitis, uveitis, rheumatoid arthritis and systemic lupus erythematosus may be treated with RNAi constructs disclosed herein. See, e.g., Samuelsson et al. 2001 Science 291:484.

FcγRIIA inhibition may also be useful in the treatment of allergic disorders and asthma. Agents that block the activity of FcγRIIA kinase may be used in treating inflammatory and allergic disorders including asthma, chronic obstructive pulmonary disease (COPD), adult respiratory distress syndrome (ARDS), ulcerative colitis, Crohn's disease, bronchitis, conjunctivitis, psoriasis, scleroderma, urticaria, dermatitis and allergic rhinitis.

FcγRIIA is expressed in platelets and mediates activation in platelets. Chacko et al. J. Biol. Chem. 271(18):10775-81, 1996. Thus inhibition of FcγRIIA may be useful in patients at risk for thrombosis, and particularly thrombosis mediated by FcγR signaling. For example, FcγRIIA inhibitors may be administered to heparinized patients to reduce the risk of heparin induced thrombocytopenia. FcγRIIA inhibitors may also be used in diabetic patients to reduce the risk of arterial thrombosis in these patients. Calverley et al. Br. J. Haemat. 121(1):139-42, 2003.

III. Formulations

The RNAi constructs disclosed herein may be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption of the constructs. The subject RNAi constructs can be provided in formulations also including penetration enhancers, carrier compounds and/or transfection agents.

Therapeutic applications of the disclosed nucleic acids can be performed with a variety of compositions and methods of administration. In view of the teachings herein, methods of administration to cells and organisms will be available to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of the agent may be required in certain cases for lasting desired effects with some diseases or disorders. Suitable dosing regimens can be determined by, for example, administering varying amounts of one or more RNAi constructs in a pharmaceutically acceptable carrier or diluent, by a pharmaceutically acceptable delivery route, and amount of agent accumulated in the body of the recipient organism can be determined at various times following administration. Similarly, the desired effect (for example, degree of suppression of transcription or expression or activity of a gene product or gene activity) can be measured at various times following administration of the RNAi construct, and this data can be correlated with other pharmacokinetic data, such as body or organ accumulation. Those of ordinary skill can determine optimum dosages, dosing regimens, and the like. Those of ordinary skill may employ $EC_{50}$ data from in vivo and in vitro animal models as guides for human studies.

The RNAi constructs disclosed herein also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to RNAi constructs and pharmaceutically acceptable salts of such RNAi constructs, and other bioequivalents. A pharmaceutical preparation will generally be free of substantial amounts of pyrogenic impurities.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66,1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For polynucleotides, examples of pharmaceutically acceptable salts include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Further, the polynucleotides can be prepared for topical, oral, local or parenteral administration. Parenteral administration, includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl (or similar) modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Electroporation may be used as a further means to introduce polynucleotides into cells. Specific approaches to delivering RNAi constructs are described in the following references: Sorensen et al. J. Mol. Biol. 327:761-766, 2003 (intravenous injection of cationic liposomes); Sioud et al. BBRC 312, 1220-1225, 2003 (intraperitoneal injection of cationic liposomes); Tompkins et al. Proc. Natl. Acad. Sci. 101:8682-8686, 2004.

Another aspect of the disclosure provides aerosols for the delivery of RNAi constructs to the respiratory tract. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung.

Administration may be accomplished by oral or nasal inhalation. Examples of pharmaceutical devices for aerosol delivery include metered dose inhalers (MDIs), dry powder inhalers (DPIs), and air-jet nebulizers. Exemplary nucleic acid delivery systems by inhalation which can be readily adapted for delivery of the subject nucleic acid constructs are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the double-stranded RNAs are described in U.S. Pat. Nos. 6,294,153; 6,344,194; 6,071,497, and PCT applications WO02/066078; WO02/053190; WO01/60420; WO00/66206. Further, methods for delivering nucleic acid constructs can be adapted from those used in delivering other oligonucleotides (e.g., an antisense oligonucleotide) by inhalation, such as described in Templin et al., *Antisense Nucleic Acid Drug Dev,* 2000, 10:359-68; Sandrasagra et al., *Expert Opin Biol Ther,* 2001, 1:979-83; Sandrasagra et al., *Antisense Nucleic Acid Drug Dev,* 2002, 12:177-81. Formulations of cationic liposomes may be used for administration by inhalation, particular after aerosolization. Nanospheres of biodegradable polymers may also be used. The deep lung, or alveoli, are the primary target of inhaled therapeutic aerosols for systemic delivery of nucleic acid constructs.

In certain embodiments, particularly where systemic dosing with the nucleic acid construct is desired, the aerosoled RNAi constructs are formulated as microparticles. Microparticles having a diameter of between 0.5 and ten microns can penetrate the lungs, passing through most of the natural barriers. A diameter of less than ten microns is required to bypass the throat; a diameter of 0.5 microns or greater is required to avoid being exhaled.

Exemplification

The invention now being generally described, it will be more readily understood by reference to the following examples, which are included merely for purposes of illustration of certain aspects and embodiments of the present invention, and are not intended to limit the invention.

EXAMPLE 1

Antibody-mediated platelet phagocytosis by human macrophages is inhibited by siRNA specific for sequences in FcγRIIA.

Study Design:
Cell Lines, Platelets, and Other Reagents
The human monoblastic cell line, THP-1 was purchased from ATCC (Manassas, Va.). Anti-HPA-1a allo-antiserum was obtained from the mother of an infant with neonatal alloimmune thrombocytopenia due to HPA-1a incompatibility. Human platelets were derived from a blood group "O" Rh$^+$ donor with the approval of the Institutional Review Board of Yale University School of Medicine.

SiRNA and Transfection
According to the Elbashir's criteria[11], siRNAs were chosen for the present study (Table 1). SiRNAs were selected so as to either hybridize only to FcγRIIA or so as to hybridize to both FcγRIIA and FcγRIIB. Sense and anti-sense RNAs were synthesized. Double strand RNAs (dsRNAs) were made followed by transfection with TransMessenger reagent according to annealing instructions from Qiagen-Xeragon, Germantown, MD. For the transfection of dsRNA, 6×10$^5$ THP-1 cells were plated into 6-well plates 24 hours prior to the transfection.

Analysis of Protein Expression
The THP-1 cellular proteins were isolated 48 hours after siRNA transfection. Northern blotting was performed to detect and quantify the levels of FcγRIIA and FcγRIIB transcripts.

Phagocytosis in Vitro Assay
Platelets at 10$^8$ cells/ml in EDTA buffer (2 mM EDTA, 0.1% BSA in PBS) were incubated in 10 um CFDA at 20° C. for 30 minutes, washed and incubated in 1:5 (V:V) test serum for 30 minutes. The platelets were washed and resuspended in M199 at 3×10$^8$/ml before exposure to THP-1 cells in a ratio of 300:1 platelets:THP-1 for 2 hours. After washing 3 times with EDTA buffer, the cells were resuspended in 1% paraformadehyde in EDTA buffer and analyzed by flow cytometry (FACScan, BD Biosciences, San Jose, (Calif.). Immediately before the FACS analysis, the surface bound fluorescence on the cells were quenched by adding 0.2% Trypan Blue[16, 17]

Results and Discussion
Cell-based Platelet Phagocytosis
Phagocytosis of antibody-coated platelets by human granulocytes in vitro was first reported by Handin et al[18]. To quantify the uptake of platelets by neutrophils, serum-treated platelets were labeled with $^{51}$Cr, and the radioactivity was measured in the washed leukocyte pellet after incubation. A phagocytosis assay of antibody sensitized platelets by primary monocytes was recently developed by using fluorescein diacetate-labeled platelets[19, 20]. However, false positive results were frequent due to non-specific binding. In this study, we employed the THP-1 cells to establish a cell-based platelet phagocytosis assay, because THP-1 cells have the ability to undergo phagocytosis and constitutively express FcγR I and IIA and IIB[21, 22]. When THP-1 cells were co-incubated with anti-HPA-1a antibody coated, CFDA-labeled platelets at 37° C., the positive population was 46%. After quenching the surface fluorescence with Trypan Blue immediately prior to analysis, the positive population was still 33%. In the control group, the co-incubation of THP-1 with CFDA-labeled, normal serum coated platelets at 37° C. in our experiments showed only 6.6% non-specific bright population, though aged platelets can be cleared by macrophage cells via a scavenger receptor[23]. This indicated that non-specific platelet phagocytosis by THP-1 cells was minimal in this assay system. Fluorescent microscopy confirmed that CFDA-labeled platelets were located in the intracellular space of cells in the sorted positive THP-1 cells. The result was reproducible in five separate experiments. Thus, this assay is reliable for quantitation of antibody-mediated platelet phagocytosis. This assay provides a useful model to study the intracellular pathway of Fc-receptor mediated platelet phagocytosis. It can also be used for clinically evaluating patients with pathologic anti-platelet antibodies as well as those with other immune diseases involving phagocytosis in the pathogenic mechanism.

RNAi down-Regulation of FcγRIIA Protein Expression
We transfected designed FcγRIIA-targeted siRNAs into THP-1 cells to test if such siRNAs can down-regulate the FcγRIIA protein expression, and also to test whether siRNAs could selectively downregulate FcγRIIA while leaving FcγRIIB relatively unaffected. Results shown in Table 2 indicate the FcγRIIA siRNA can specifically knockdown FcγRIIA transcript expression in vitro.

Figure 3:
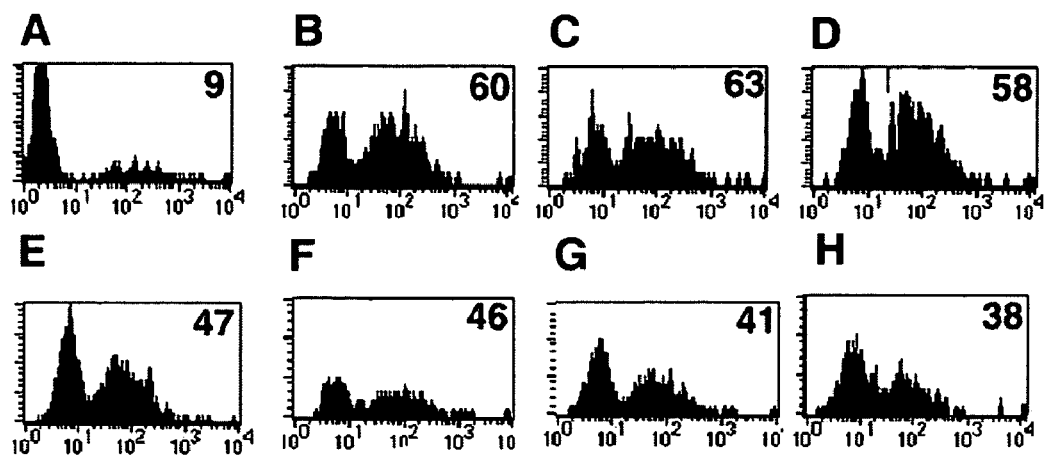
FIG. 3: FcγRIIA-speicifc siRNA inhibited antibody mediated platelet phagocytosis.

Inhibition of Anti-Platelet Antibody-Mediated Platelet Phagocytosis by THP-1 Cells by FcγRIIA dsRNAs
Based on above results, we then tested whether or not FcγRIIA dsRNAs could interfere with the phagocytotic function of THP-1 cells. FIG. 3 shows that FcγRIIA dsRNA treated THP-1 cells decreased the ability to ingest antibody-coated platelets substantially. These results indicate that FcγRIIA is important for antibody-mediated platelet phagocytosis. Targeting FcγRIIA is expected to be a potential pharmacologic intervention for immune thrombocytopenia. Targeting FcγRIIA with siRNA may also be applied to other disease condition of antibody-mediated phagocytosis. Moreover, knockdown of a given gene with siRNAs combining a cell-based assay system offers an important strategy for human functional genomics, like the studies of gene function in gene knockout animals. In conclusion, we report that FcγRIIA siRNA specifically inhibits antibody-mediated platelet phagocytosis in human system in vitro.

TABLE 2

FcγRIIA Target Sequences and Effects on Phagocytosis

| Probe: | Sequence | SEQ ID NO: | Effect on mRNA | Effect on phagocytosis |
|---|---|---|---|---|
| CD32IIA-A | AAACTTGAGCCCCCGTGGATC | (SEQ ID NO:2) | 0 | 0 |
| CD32IIA-B | AATTTGAGCCACCTGGACGTC | (SEQ ID NO:3) 0 | 0 | 0 |

TABLE 2-continued

FcγRIIA Target Sequences and Effects on Phagocytosis

| Probe: | Sequence | SEQ ID NO: | Effect on mRNA | Effect on phagocytosis |
|---|---|---|---|---|
| CD32IIA-C | AAAGAGACAACTTGAAGAAAC | (SEQ ID NO:4) | + | + |
| CD32IIA-D | AAACCATCATGCTGAGGTGCC | (SEQ ID NO:5) | + | 0 |
| CD32IIA-E | AACCATCATGCTGAGGTGCCA | (SEQ ID NO:6) | +++ | + |
| CD32IIA-F | AAATTCTCCCGTTTGGATCCC | (SEQ ID NO:7) | +++ | + |
| CD32IIA-G | AATTCTCCCGTTTGGATCCCA | (SEQ ID NO:8) | + | ++ |
| CD32IIA-H | AAACCCGCCTCCCAGGTTTAA | (SEQ ID NO:9) | +++ | ++ |
| CD32IIA-I | AACTTCTGGCCTCTAGCGATC | (SEQ ID NO:10) | ++ | nt |
| CD32IIA-J | AAGTGCTGGGATGACCAGCAT | (SEQ ID NO:11) | ++ | nt |
| CD32IIA-K | AATGTCCAGCCTCTTTAACAT | (SEQ ID NO:12) | ++ | nt |
| CD32IIA-L | AACATCTTCTTTCCTATGCCC | (SEQ ID NO:13) | ++ | nt |

Key:
"0" = <10% inhibition
"+" = 10-30% inhibition
"++" = 31-60% inhibition
"+++" = >60% inhibition
"nt" = not tested Reference List for Example 1:

1. Beardsley D S. Pathophysiology of immune thrombocytopenic purpura. Blood Reviews. 2002; 16:13-14.
2. Cines D B, Blanchette V S. Immune thrombocytopenic purpura. New England Journal of Medicine. 2002; 346:995-1008.
3. Greenberg S, Grinstein S. Phagocytosis and innate immunity. Current Opinion in Immunology. 2002; 14:136-145.
4. Cox D, Greenberg S. Phagocytic signaling strategies: Fc(gamma)receptor mediated phagocytosis as a model system. Seminars in Immunology. 2001; 13:339-345.
5. Indik Z K, Park J G, Hunter S, Schreiber A D. The molecular dissection of Fc gamma receptor mediated phagocytosis. Blood. 1995; 86:4389-4399.
6. Crowley M T, Costello P S, Fitzer-Attas C J, et al. A critical role for Syk in signal transduction and phagocytosis mediated by Fcgamma receptors on macrophages. Journal of Experimental Medicine. 1997; 186:1027-1039.
7. Kiefer F, Brumell J, Al Alawi N, et al. The Syk protein tyrosine kinase is essential for Fcgamma receptor signaling in macrophages and neutrophils. Molecular & Cellular Biology. 1998; 18:4209-4220.
8. Matsuda M, Park J G, Wang D C, Hunter S, Chien P, Schreiber A D. Abrogation of the Fc gamma receptor IIA-mediated phagocytic signal by stem-loop Syk antisense oligonucleotides. Molecular Biology of the Cell. 1996; 7:1095-1106.
9. Hannon G J. RNA interference. Nature. 2002; 418:244-251.
10. Plasterk R H. RNA silencing: the genome's immune system. Science. 2002; 296: 1263-1265.
11. Elbashir SM, Harborth J, Lendeckel W, Yalcin A, Weber K, Tuschl T. Duplexes of 21-nucleotide RNAs mediate RNA interference in cultured mammalian cells. [comment].—Nature.-2001;411:494-498.
12. Semizarov D, Frost L, Sarthy A, Kroeger P, Halbert D N, Fesik S W. Specificity of short interfering RNA determined through gene expression signatures. [comment]. Proceedings of the National Academy of Sciences of the United States of America. 2003; 100:6347-6352.
13. Hutvagner G, McLachlan J, Pasquinelli A E, Balint E, Tuschl T, Zamore P D. A cellular function for the RNA-interference enzyme Dicer in the maturation of the let-7 small temporal RNA.[comment]. Science. 2001; 293:834-838.
14. Caplen N J, Parrish S, Imani F, Fire A, Morgan R A. Specific inhibition of gene expression by small double-stranded RNAs in invertebrate and vertebrate systems. Proceedings of the National Academy of Sciences of the United States of America. 2001; 98:9742-9747.
15. Ghazizadeh S, Bolen J B, Fleit H B. Tyrosine phosphorylation and association of Syk with Fc gamma RII in monocytic THP-1 cells. Biochemical Journal. 1995; 305: 669-674.
16. Lehmann A K, Somes S, Halstensen A. Phagocytosis: measurement by flow cytometry. Journal of Immunological Methods 2000; 243:229-242.
17. Ramet M, Manfruelli P, Pearson A, Mathey-Prevot B, Ezekowitz R A. Functional genomic analysis of phagocytosis and identification of a *Drosophila* receptor for *E. coli*. Nature. 2002; 416:644-648.
18. Handin R1, Stossel T P. Phagocytosis of antibody-coated platelets by human granulocytes. New England Journal of Medicine. 1974; 290:989-993.
19. Lim J, Kim Y, Han K, et al. Flow cytometric monocyte phagocytic assay for predicting platelet transfusion outcome. Transfusion. 2002; 42:309-316.
20. Wiener E, Abeyakoon O, Benchetrit G, Lyall M, Keler T, Rodeck C H. AntiHPA-1a-mediated platelet phagocytosis by monocytes in vitro and its inhibition by Fc gamma receptor (FcgammaR) reactive reagents. European Journal of Haematology. 2003; 70:67-74.

21. Tsuchiya S, Yamabe M, Yamaguchi Y, Kobayashi Y, Konno T, Tada K. Establishment and characterization of a human acute monocytic leukemia cell line (THP1). International Journal of Cancer. 1980; 26:171-176.

22. Garcia-Garcia E, Rosales R, Rosales C. Phosphatidylinositol 3-kinase and extracellular signal-regulated kinase are recruited for Fc receptor-mediated phagocytosis during monocyte-to-macrophage differentiation. Journal of Leukocyte Biology. 2002; 72:107-114.

23. Brown S B, Clarke M C, Magowan L, Sanderson H, Savill J. Constitutive death of platelets leading to scavenger receptor-mediated phagocytosis. A caspaseindependent cell clearance program. Journal of Biological Chemistry. 2000; 275:5987-5996.

What is claimed is:

1. An isolated RNAi construct for inhibiting the expression of FcγRIIA wherein the isolated RNAi construct comprises:
   (a) a sense polynucleotide strand comprising, contiguously, the sequence AAACCCGCCTCCCAGGTTTAA (SEQ ID NO: 9); and
   (b) an antisense polynucleotide strand that hybridizes to said sense polynucleotide strand, wherein the antisense polynucleotide strand and the sense polynucleotide strand form a duplex consisting of 21 to about 30 base pairs in length and the isolated RNAi construct inhibits FcγRIIA expression.

2. The isolated RNAi construct of claim 1, wherein the isolated RNAi construct is a hairpin nucleic acid.

3. A composition comprising a pharmaceutically acceptable carrier and an isolated RNAi construct that inhibits expression of FcγRIIA, wherein the isolated RNAi construct comprises, contiguously, the sequence AAACCCGCCTC-CCAGGTTTAA (SEQ ID NO: 9).

4. The composition of claim 3, wherein the isolated RNAi construct comprises:
  (a) an antisense polynucleotide strand that is capable of hybridizing to at least a portion of a FcγRIIA transcript and inhibits FcγRIIA expression; and,
  (b) a sense polynucleotide strand that hybridizes to said antisense polynucleotide strand.

5. The composition of claim 4, wherein greater than 50% of the nucleotides of the antisense polynucleotide strand are RNA.

6. The composition of claim 4, wherein the antisense polynucleotide strand comprises one or more modifications selected from the group consisting of:
  (a) a modification to the sugar-phosphate backbone;
  (b) a modification to the base portion of a nucleotide; and
  (c) a conjugated hydrophobic moiety.

7. The composition of claim 4, wherein the sense polynucleotide strand comprises one or more modifications selected from the group consisting of:
  (a) a modification to the sugar-phosphate backbone;
  (b) a modification to the base portion of a nucleotide; and
  (c) a conjugated hydrophobic moiety.

8. The isolated RNAi construct of claim 1, wherein the construct does not substantially inhibit FcγRIIB expression.

* * * * *